United States Patent [19]

Geck et al.

[11] Patent Number: 5,712,343
[45] Date of Patent: Jan. 27, 1998

[54] PREPARATION OF ORGANOPOLYSILOXANE MICROEMULSIONS

[75] Inventors: Michael Geck, Burghausen; Hans-Juergen Lautenschlager, Haiming; Bernward Deubzer, Burghausen; Petra Stinglhammer, Simbach; Peter Habereder, Krailling; Kurt Ullrich, Burghausen, all of Germany

[73] Assignee: Wacker-Chemie GmbH, Munich, Germany

[21] Appl. No.: 633,353

[22] Filed: Apr. 17, 1996

Related U.S. Application Data

[63] Continuation of Ser. No. 287,311, Aug. 8, 1994, abandoned.

[30] Foreign Application Priority Data

Aug. 27, 1993 [DE] Germany ............... 43 28 917.7

[51] Int. Cl.[6] ............... C08L 83/00; B01J 13/00
[52] U.S. Cl. ............... 524/837; 524/838; 524/864; 252/312; 252/314; 252/321; 252/356; 252/DIG. 1; 106/287.14
[58] Field of Search ............... 524/837, 838, 524/864; 252/312, 321, 314, 356, DIG. 1; 106/287.14

[56] References Cited

U.S. PATENT DOCUMENTS

| 5,057,572 | 10/1991 | Chrobaczek et al. | 524/588 |
| 5,073,593 | 12/1991 | Ozaki et al. | 524/767 |
| 5,133,897 | 7/1992 | Balzer | 252/312 |
| 5,268,126 | 12/1993 | Balzer | 252/312 |
| 5,302,657 | 4/1994 | Huhn et al. | 524/588 |

FOREIGN PATENT DOCUMENTS

| 0138192 | 4/1985 | European Pat. Off. . |
| 0404027 | 12/1990 | European Pat. Off. . |
| 0442098 | 8/1991 | European Pat. Off. . |
| 0532256 | 3/1993 | European Pat. Off. . |

*Primary Examiner*—Karen A. Dean

[57] ABSTRACT

The invention relates to the preparation of organopolysiloxane microemulsions, wherein the components (A) organopolysiloxane, (B) emulsifier, (C) water, optionally, (D) cosurfactant and optionally (E) acid are brought together and mixed in any desired sequence. Microemulsions are formed spontaneously without introduction of energy in the form of heat or severe shearing forces.

21 Claims, No Drawings

PREPARATION OF ORGANOPOLYSILOXANE MICROEMULSIONS

This is a continuation of application Ser. No. 08/287,311 filed on Aug. 8, 1994, now abandoned.

FIELD OF THE INVENTION

The present invention relates to a process for the preparation of organopolysiloxane microemulsions in which the components are brought together and mixed in any desired sequence.

BACKGROUND OF INVENTION

The preparation of finely divided organopolysiloxane emulsions and microemulsions is already known.

According to EP-A 138 192, an oil concentrate is formed from organopolysiloxane, emulsifier and water in a first step and has to be dispersed in water very rapidly and without a time delay in a second step so that a sufficiently finely divided dispersion is obtained.

According to EP-A 532 256, for the preparation of transparent microemulsions of amino-functional organopolysiloxanes it is necessary to prepare a mixture of silicone oil and emulsifier in a first step and a homogeneous concentrated mixture therefrom by addition of a little water in a second step, this mixture being diluted with water in a third step and an acid being added in a fourth step.

U.S. Pat. No. 5,073,593 describes the preparation of a microemulsion of a specific amino-functional polysiloxane in which a mixture of oil, nonionic emulsifier and glycol is prepared, acid and a little water being added in a second stage; a concentrated precursor emulsion is formed therefrom and is then dispersed in water.

The processes according to EP-A 138 192, EP-A 532 256 and U.S. Pat. No. 5,073,593 have the common feature that, before preparation of the actual microemulsion, a concentrate of oil, emulsifier(s), further additives and a little water must first be prepared, thus several preparation steps must be carried out and there is a certain sequence for stirring together the constituents of the microemulsion.

In the preparation of finely divided silicone emulsions based on aminoalkyl-substituted polysiloxanes according to U.S. Pat. No. 5,057,572 from silicone oil, emulsifier(s), water and acid, it is indeed not necessary to prepare a concentrate beforehand; however, it is essential to heat the mixture of the components for preparation of the finely divided emulsion to at least 50° C.

SUMMARY OF INVENTION

The object of the present invention was to provide stable organopolysiloxane microemulsions by a process which is easy to carry out, in particular, no concentrate has to be prepared, no sequence of addition of the components has to be observed and no heating is necessary.

The present invention relates to a process for the preparation of organopolysiloxane microemulsions in which the components (A) organopolysiloxane, (B) emulsifier, (C) water, optionally, (D) cosurfactant and optionally (E) acid are brought together and mixed in any desired sequence.

The organopolysiloxane microemulsions prepared are transparent to water-clear and preferably have average particle sizes of not more than 50 nm, in particular not more than 20 nm. These microemulsions are thermodynamically stable and form spontaneously. In contrast to the opinion of experts, introduction of energy in the form of heat or severe shearing forces is not necessary during the preparation. Mixing is carried out merely to bring the components into contact with one another and to obtain a homogeneous organopolysiloxane microemulsion. The amounts of energy introduced into the organopolysiloxane microemulsions during mixing are very low. For example, one liter of microemulsion can be prepared with a laboratory magnetic stirrer with an output of 2 watt, while conventional processes require high stirrer outputs, such as rotor/stator mixers having an output of about 450 watt, or at least blade stirrers with an output of about 26 watt in order to prepare 1 liter of organopolysiloxane microemulsion.

The individual components employed in the process can comprise a single constituent or a mixture of various constituents. For example, a mixture of various emulsifiers can be employed as components B.

The microemulsions are of the oil-in-water type which have a discontinuous oily phase which contains the organopolysiloxanes A and a continuous aqueous phase.

The organopolysiloxanes (A) which are processed to a microemulsion in the process preferably comprise at least one amino-functional organopolysiloxane. Preferably, at least 50% by weight, in particular at least 75% by weight, of the organopolysiloxane comprises amino-functional organopolysiloxanes.

Organopolysiloxanes (A) which are preferably employed in the process are organopolysiloxanes of the formula

$$R_nR'_mSiO_{(4-n-m)/2} \qquad (I)$$

wherein

R are identical or different, optionally substituted hydrocarbon radicals or hydrocarbonoxy radicals having in each case, 1 to 18 carbon atoms, R' are identical or different Si-C-bonded substituted hydrocarbon radicals containing polar groups, or hydroxyl groups, n is an integer having a value of 0, 1, 2 or 3 and m is an integer having a value of 0, 1, 2 or 3, and the sum of n+m has an average value of 1.8 to 2.2 and m is chosen such that the polyorganosiloxane contains at least one radical R'.

Although not shown in formula (I), some of the radicals R can be replaced by hydrogen atoms bonded directly to silicon atoms. However, this is not preferred.

The sum of n+m preferably has an average value of 1.9 to 2.1.

Examples of hydrocarbon radicals R are alkyl radicals, such as the methyl, ethyl, n-propyl, iso-propyl, n-butyl, iso-butyl, tert-butyl, n-pentyl, iso-pentyl, neo-pentyl and tert-pentyl radical; hexyl radicals, such as the n-hexyl radical; heptyl radicals, such as the n-heptyl radical; octyl radicals, such as the n-octyl radical and iso-octyl radicals, such as the 2,2,4-trimethylpentyl radical; nonyl radicals, such as the n-nonyl radical; decyl radicals, such as the n-decyl radical; dodecyl radicals, such as the n-dodecyl radical; octadecyl radicals, such as the n-octadecyl radical; alkenyl radicals, such as the vinyl, allyl and the 5-hexen-1-yl radical; cycloalkyl radicals, such as cyclopentyl, cyclohexyl and cycloheptyl radicals and methylcyclohexyl radicals; aryl radicals, such as the phenyl, naphthyl and anthryl and phenanthryl radicals; alkaryl radicals, such as o-, m- and p-tolyl radicals, xylyl radicals and ethylphenyl radicals; and aralkyl radicals, such as the benzyl radical and the α- and the β-phenylethyl radical.

Examples of substituted radicals R are cyanoalkyl radicals, such as the β-cyanoethyl radical, and halogenated hydrocarbon radicals, for example halogenoalkyl radicals, such as the 3,3,3-trifluoro-n-propyl radical, the 2,2,2,2',2', 2'-hexafluoroisopropyl radical and the heptafluoroisopropyl radical, and halogeno- aryl radicals, such as the o-, m- and p-chlorophenyl radical.

Examples of optionally substituted hydrocarbonoxy radicals R are substituted and unsubstituted hydrocarbon radicals R according to the above mentioned examples bonded via an oxygen atom directly to a silicon atom, in particular alkoxy radicals having 1 to 18 carbon atoms and phenoxy radicals, specifically the methoxy, ethoxy, n-propoxy, iso-propoxy and phenoxy radical. Preferably not more than 5% of the radicals R are optionally substituted hydrocarbonoxy radicals.

Examples of radicals R' are amino-functional hydrocarbon radicals, for example aminoalkyl radicals, such as the γ-aminopropyl radical and the β-aminoethyl-γ-aminopropyl radical; aminoaryl radicals; Si-C-bonded cyclic amino-functional radicals; amido-functional radicals, such as the γ-acetamidopropyl radical, and partly or completely acetylated β-aminoethyl-γ-aminopropyl radicals; hydroxyl groups, and carboxylic acid or sulfonic acid radicals, or esters thereof, bonded to the silicon atom via an alkylene or arylene group; mercaptoalkyl radicals; and Si-C-bonded hydrocarbon radicals which contain epoxide, hydroxyl, amido and/or carboxyl groups.

Preferably, the radical R' is an amino-functional radical.

Examples of preferred amino-functional radicals R' are radicals of the formula $$-R^1-[NR^2(CH_2)_a]_b NHR^2,\qquad (II),$$

in which

R$^1$ is a divalent C$_1$- to C$_{18}$-hydrocarbon radical,

R$^2$ is a hydrogen atom or an optionally substituted C$_1$-to C$_{18}$-hydrocarbon radical, a has the values 2, 3, 4, 5 or 6 and b has the values 0, 1, 2, 3 or 4.

Examples of divalent C$_1$- to C$_{18}$-hydrocarbon radicals R$^1$ are saturated straight-chain, branched or cyclic alkylene radicals, such as the methylene and ethylene radical, and propylene, butylene, pentylene, hexylene, 2-methylpropylene, cyclohexylene and octadecylene radicals, or unsaturated alkylene or arylene radicals, such as the hexenylene radical and phenylene radicals, the n-propylene radical and the 2-methylpropylene radical being particularly preferred.

Examples of the optionally substituted C$_1$- to C$_{18}$-hydrocarbon radicals R$^2$ are the examples given for R.

Preferably, in the above formula (II),

R$^1$ is a divalent C$_2$- to C$_6$-hydrocarbon radical,

R$^2$ is a hydrogen atom or a methyl or cyclohexyl radical, a has the values 2 or 3 and b has the values 0 or 1.

Linear polydimethylsiloxanes, which contain not more than 5% of C$_1$- to C$_3$-alkoxy or hydroxyl end groups as radicals R, in addition to methyl radicals, are more preferred. These polydimethylsiloxanes preferably contain, as radicals R', the radicals H$_2$N(CH$_2$)$_3$—, H$_2$N(CH$_2$)$_2$NHCH$_2$CH(CH$_3$)CH$_2$—, H$_2$N(CH$_2$)$_3$—,

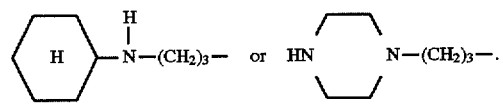

The radicals R are preferably methyl, ethyl, phenyl, methoxy and/or vinyl radicals. Because of easier accessibility, preferably 50% of the radicals R, in particular at least 80% of the radicals R, are methyl radicals.

The organopolysiloxane (A) employed in the process is preferably liquid. In particular, the organopolysiloxanes employed in the process have viscosities of 100 mPa.s to 50,000 mPa.s, measured at 25° C.

If an amino-functional organopolysiloxane (A) is employed, it is preferable to have an amine number of 0.05 to 3.0, in particular 0.1 to 1.0. The amine number of an amino-functional substance is determined as the consumption in cm$^3$ of 1N hydrochloric acid during titration of 1 g of the amino-functional substance.

The following emulsifiers B are particularly suitable for use in the process:

1. Alkyl sulfates, having a chain length of 8–18 C atoms, and alkyl ether-sulfates having 8–18 C atoms in the hydrophobic radical and 1–40 ethylene oxide (EO) or propylene oxide (PO) units.
2. Sulfonates such as alkylsulfonates having 8–18 C atoms, alkylaryl sulfonates having 8–18 C atoms and esters and half-esters of sulfosuccinic acid with monohydric alcohols or alkylphenols having 4–15 C atoms; these alcohols or alkylphenols can also be ethoxylated with 1–40 EO units.
3. Alkali metal and ammonium salts of carboxylic acids and poly-(alkylene glycol) ether-carboxylic acids having 8–20 C atoms in the alkyl, aryl, alkaryl or aralkyl radical and 1–40 EO or PO units.
4. Phosphoric acid partial esters and alkali metal and ammonium salts thereof, such as alkyl and alkaryl phosphates having 8–20 C atoms in the organic radical and alkyl ether- and alkaryl ether-phosphates having 8–20 C atoms in the alkyl or alkaryl radical and 1–40 EO units.
5. Alkyl polyglycol ethers having 2–40 EO units and alkyl radicals of 4–20 C atoms.
6. Alkylaryl polyglycol ethers having 2–40 EO units and 8–20 C atoms in the alkyl and aryl radicals.
7. Ethylene oxide/propylene oxide (EO/PO) block copolymers having 8–40 EO and PO units.
8. Fatty acid polyglycol esters having 6–24 C atoms and 2–40 EO units.
9. Alkyl polyglycosides of the formula $$R''-O-Z_o \qquad (III),$$

in which

R'' is a linear or branched, saturated or unsaturated alkyl radical having on average 8–24 C atoms and Z$_o$ is an oligoglycoside radical having on average o=1–10 hexose or pentose units, or mixtures thereof.

10. Linear organopolysiloxanes containing polar groups and having alkoxy groups and up to 24 C atoms and/or up to 40 EO and/or PO groups.
11. Salts of primary, secondary and tertiary fatty amines having 8–24 C atoms with acetic acid, sulfuric acid, hydrochloric acid and phosphoric acids.
12. Quaternary methylalkyl and methylalkylbenzylammonium salts, the alkyl groups of which have 6–24 C atoms, in particular the halides, sulfates, phosphates, acetates and hydroxides.

13. Alkylpyridinium, alkylimidazolinium and alkyloxazolinium salts, the alkyl chain of which has up to 18 C atoms, specifically in the form of their halides, sulfates, phosphates and acetates.

The use of several emulsifiers is preferred.

Preferred emulsifiers are the nonionic emulsifiers listed above under 5, 6 and 9, especially the alkyl polyglycol ethers listed under 5, specifically alkyl polyglycol ethers having 2–20 EO units and alkyl radicals of 4–20 C atoms, and the alkyl polyglycosides listed under 9, having a saturated alkyl radical with an average 8–14 C atoms and an average degree of glycosidation n of between 1.1 and 3.

Cosurfactants D can be employed to reduce the particle size and to reduce the amount of emulsifiers B required.

Cosurfactants D are understood as meaning polar compounds of average molecular weight, such as $C_3$ to $C_8$ alcohols, suitable diand polyols, amines, esters and ketones.

Examples of suitable cosurfactants D are 1-propanol, 2-propanol, 1-butanol, 2-butanol, 2-methyl-2-propanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 3-octanol and 4-octanol; glycerol, 1,2-butanediol, 1,3-butanediol and 1,2-hexanediol; 1-aminobutane, 2-aminobutane, 2-amino-2-methylpropane, 1-aminopentane, 2-aminopentane, 1-aminohexane, 1-aminoheptane and 1-aminooctane; ethyl, propyl, isopropyl, butyl, isobutyl, pentyl, isopentyl and hexyl acetate; methyl, ethyl and tert-butyl propionate; methyl, ethyl, propyl and butyl butyrate; and 2-butanone, 2-pentanone, 3-pentanone, 4-methyl-2-pentanone, 2-hexanone, 3-hexanone, 2-heptanone, 3-heptanone, 4-heptanone, 5-methyl-3-heptanone, 2-octanone and 3-octanone.

Examples of preferred cosurfactants D are 1-alkanols of the above mentioned examples having $C_5$- to $C_8$-chains, glycerol, propyl, butyl and pentyl acetate and 2-pentanone.

More preferred cosurfactants D are 1-pentanol, 1-hexanol, 1-octanol and glycerol.

Acids E can be employed in the process to establish a desired pH or to form acid addition salts with another component. The use of acids is preferred if organopolysiloxanes A of the above formula (I) in which the R' are amino-functional radicals are used.

Examples of mineral acids which can be reacted with the above mentioned amino-functional hydrocarbon radicals R' to give the corresponding ammonium-functional radicals are hydrochloric, perchloric, sulfuric, sulfurous, nitric, nitrous, hydrofluoric, phosphoric, diphosphoric and polyphosphoric acids. Examples of suitable carboxylic acids are formic, acetic, propionic and butanoic acids, citric acid, trichloro-, dichloro- and chloroacetic acid, trifluoroacetic acid, cyanoacetic acid, phenylacetic acid, benzoic acid, m- and p-nitrobenzoic acid, oxalic acid, malonic acid and lactic acid.

Acetic acid and formic acid are more preferred.

In addition to the components of organopolysiloxane A, emulsifier B, water C, cosurfactant D and acid E, additives F can also be used in the process. The additives F are, in particular, bactericides, fungicides, algicides, microbicides, fragrances, corrosion inhibitors, dyestuffs, pigments, thickeners and fillers.

The proportions of the organopolysiloxane A as the oily phase in the continuous aqueous phase can be varied within wide ranges, depending on the solids content required in the microemulsions. Preferably, 5% to 60% by weight, in particular 10% to 40% by weight, of organopolysiloxane A, 1% to 30% by weight, in particular 2% to 25% by weight, of emulsifier B, 0% to 15% by weight, in particular 0% to 10% by weight, of cosurfactant D, 0% to 3% by weight, in particular 0% to 1.5% by weight, of acid E and 0% to 3% by weight, in particular 0% to 1.5% by weight, of additives F, based on the total weight of the microemulsion, are employed, the remainder comprising water C. The proportion of water C is preferably at least 31% by weight.

Mixing of components A to F is carried out in a variable sequence by stirring without introduction of shearing forces by blade, beam, anchor and grid stirrers, and in small batches, by a glass rod or spatula or by shaking.

The pressure exerted on the mixture of components during mixing is preferably atmospheric pressure; the prevailing room temperature is preferably 10° C. to 30° C., increased or reduced, by thermodynamic processes during the mixing operations.

In a preferred embodiment of the process, aminofunctional organopolysiloxane (A), emulsifier(s) (B), water (C), optionally cosurfactant(s) (D), optionally acid (E) and additive(s) (F) are mixed by stirring or shaking. Mixing can be carried out in a variable sequence. If several organopolysiloxanes (A1, A2, . . .), emulsifiers (B1, B2, . . .), cosurfactants (D1, D2, . . .), acids (E1, E2 . . .) and/or additives (F1, F2, . . .) are employed, the sequence can be varied, for example, water, oil A1, cosurfactant D1, oil A2 and emulsifier B2 are added to emulsifier B1 or, cosurfactant D1, emulsifier B1, water, emulsifier B2 and oil A2 are added to oil A1, or other sequences are chosen. The water added can be added in one portion, or it can be added in several portions at various points of the addition of components.

The components are preferably added successively, but can also be metered in simultaneously. The mixture is preferably stirred during addition of the components or shaken briefly after each addition of component, but this is not necessary; thorough mixing can also take place for the first time after all the components have been metered in.

If the components are added in succession, it is not necessary to observe certain stirring or standing times after addition of individual or certain components and/or before addition of further components; all of the components can be metered in and mixed without delay. However, the addition of the various components can also be separated by stirring or standing times of a few minutes to a few months. It is preferably to observe stirring or standing times of 5 minutes to 24 hours after metering in the last of the components contained in the microemulsions.

The microemulsions can be employed in all instances where silicone emulsions and microemulsions have also been employed to date. They are particularly suitable as agents or as a constituent of a composition for impregnating fibers and woven fabrics, in cosmetics and cleaning and polishing compositions, in paints or impregnating compositions for building materials and precursors thereof, in antifoam compositions and for coatings which repel tacky substances. They can also be used for sizing fibers of glass, ceramics and carbon, for impregnating and coating textile fibers, for example as a thread lubricant, and textile fabrics, in cosmetics, such as handcreams, body lotions, shampoos, hair rinses, hair setting lotions and shaving creams and lotions, in polishes, such as furniture, floor and car polishes, in waxes, such as floor waxes, and in disinfectants, for rendering gypsum hydrophobic before or after shaping thereof to give components, for impregnating natural or artificial rock, concrete, cement or masonry, for rendering gas concrete hydrophobic before or after foaming thereof, in paints for buildings and components thereof, such as emulsion paints, in particular in silicone paints, in or as paper coatings for carriers of self-adhesive labels and as mold release agents for polymers.

The use of the microemulsions, in particular the microemulsions of amino-functional organopolysiloxanes A, as agents or in compositions for impregnating and coating textile fibers and fabrics is particularly preferred. The microemulsions thus impart, to the textile fibers and sheet-like structures treated with them, for example, a pleasant, soft handle.

EXAMPLES

In the examples which follow, unless stated otherwise, all the amounts and percentages are based on the weight. Unless stated otherwise, the following examples are carried out under atmospheric pressure (about 0.1 mPa (abs)) and at room temperature of about 20° C. or at temperatures and pressures which are established when the reactants are brought together at room temperature without additional heating or cooling or due to the action of mixing apparatuses on the components or mixtures.

Amino-functional organopolysiloxanes A

A1 organopolysiloxane comprising dimethylsiloxymethyl(N-[2-aminoethyl]-3-aminopropyl) siloxy units and terminal methoxy-dimethylsilyl groups; viscosity: 1200 mPa.s at 25° C.; amine number: 0.6.

A2 Organopolysiloxane comprising dimethylsiloxymethyl(N-[2-aminoethyl]-3-aminopropyl) siloxy units and terminal methoxy-dimethylsilyl groups; viscosity: 1000 mPa.s at 25° C.; amine number: 0.3

A3 Organopolysiloxane comprising dimethylsiloxymethyl(N-[2-aminoethyl]-3-aminopropyl) siloxy units and terminal methoxy-dimethylsilyl groups; viscosity: 6500 mPa.s at 25° C.; amine number: 0.13.

A4 Organopolysiloxane comprising dimethylsiloxymethyl-(N-cyclohexyl-3-aminopropyl) siloxy units and terminal trimethylsilyl groups; viscosity: 1000 mPa.s at 25° C.; amine number: 0.3.

Emulsifiers (B)

B1 Isotridecyl ethoxylate having on average 8 ethylene oxide units.

B2 Isotridecyl ethoxylate having on average 6 ethylene oxide units.

B3 n-Butyl ethoxylate having 2 ethylene oxide units.

B4 $C_8/C_{11}$-Alkyl polyglycoside having a degree of glycosidation of 1.35 (50% strength in water).

EXAMPLE 1

Preparation of a microemulsion of 30 parts by weight of polysiloxane A1, 10 parts by weight of emulsifier B1, 15 parts by weight of emulsifier B3, 45 parts by weight of water (C) and 0.57 part by weight of glacial acetic acid (E).

After the first component has been initially introduced into the mixing vessel, the other components were added in succession without delay. After each addition of component, the mixture was shaken or stirred for about 15 seconds. After addition of the last component, the mixture was left to stand for 30 minutes.

The following sequences of bringing the microemulsion constituents together were implemented:

a. initial introduction of B1; addition of B3, C, E and A1.

b. initial introduction of B1; addition of B3, E, A1 and C.

c. initial introduction of E; addition of A1, B1, B3 and C.

d. initial introduction of B1; addition of B3, C, A1 and E.

e. initial introduction of B3; addition of B1, A1, E and C.

f. initial introduction of A1; addition of E, B1, B3 and C.

g. initial introduction of C; addition of B1, B3, A1 and E.

h. initial introduction of C; addition of B1, B3, E and A1.

In all cases, water-clear microemulsions were obtained. "Particle sizes" could not be determined in any case (measured with an Autosizer 2 C from Malvern), since the particles were too small (<<10 nm). The microemulsions were storage-stable for longer than 3 months, but started to discolor to a slightly yellowish color after standing time of about 1 week.

EXAMPLE 2

Preparation of microemulsion from 15 parts by weight of polysiloxane A1, 5 parts by weight of emulsifier B3, 30 parts by weight of emulsifier B4 (50% strength in water), 50 parts by weight of water (C) and 0.28 parts by weight of glacial acetic acid (E).

After the first component had been initially introduced into the mixing vessel, the other components were added in succession without delay. After each addition of component, the mixture was shaken or stirred for about 15 seconds. After addition of the last component, the mixture was left to stand for an hour.

The following sequences of bringing the microemulsion constituents together were implemented:

a. initial introduction of B4; addition of B3, C, E and A1.

b. initial introduction of B3; addition of B4, E, A1 and C.

c. initial introduction of C; addition of E, B4, B3 and A1.

In all cases, water-clear microemulsions colored brown-yellow by the intrinsic color of emulsifier B4 were obtained. The "particle sizes" were <20 nm (measured with an Autosizer 2 C from Malvern). The microemulsions were storage-stable for longer than 3 months.

EXAMPLE 3

Preparation of a microemulsion from 15 parts by weight of polysiloxane A2, 10 parts by weight of emulsifier B2, 70 parts by weight of water (C), 5 parts by weight of glycerol (D) and 0.16 part by weight of glacial acetic acid (E).

After the first component was initially introduced into the mixing vessel, the other components were added in succession without delay. After each addition of component, the mixture was shaken or stirred for about 15 seconds. After addition of the last component, the mixture was left to stand for an hour.

The following sequences of bringing the microemulsion constituents together were implemented:

a. initial introduction of B2; addition of D, C, E and A2.

b. initial introduction of C; addition of B2, D, A2 and E.

c. initial introduction of C; addition of B2, A2, E and D.

In all cases, water-clear microemulsions were obtained. The "particle sizes" were in all cases <20 nm (measured with an autosizer 2 C from Malvern). The microemulsions were storage-stable for longer than 6 months.

EXAMPLE 4

Preparation of a microemulsion from 15 parts by weight of polysiloxane A3, 15 parts by weight of emulsifier B2, 5 parts by weight of emulsifier B3, 65 parts by weight of water (C) and 0.07 parts by weight of glacial acetic acid (E).

After the first component was initially introduced into the mixing vessel, the other components were added in succession without delay. After each addition of component, the mixture was shaken or stirred for about 15 seconds. After addition of the last component, the mixture was left to stand for an hour.

The following sequences of bringing the microemulsion constituents together were implemented:

a. initial introduction of B2; addition of B3, C, E and A3.
b. initial introduction of B2; addition of B3, E, A3 and C.
c. initial introduction of C; addition of E, B2, B3 and A3.

In cases a and c, water-clear microemulsions were obtained, and in base b, a transparent microemulsion was obtained. The microemulsions were storage-stable for longer than 3 months.

EXAMPLE 5

Preparation of a microemulsion from 20 parts by weight of polysiloxane A4, 15 parts by weight of emulsifier B2, 10 parts by weight of emulsifier B3, 55 parts by weight of water (C) and 0.32 part by weight of formic acid (E), 85% strength.

After the first component was initially introduced into the mixing vessel, the other components were added in succession without delay. After each addition of component, the mixture was shaken or stirred for about 15 seconds. After addition of the last component, the mixture was left to stand for 30 minutes.

The following sequences of bringing the microemulsion constituents together were implemented:

a. initial introduction of B2; addition of B3, C, E and A4.
b. initial introduction of B2; addition of B3, E, A4 and C.
c. initial introduction of A4; addition of E, B2, B3 and C.

In all cases, clear to slightly transparent microemulsions were obtained. The "particle size" was in all cases <50 nm (measured with an autosizer 2 C from Malvern).

What is claimed:

1. A process for the preparation of an organopolysiloxane microemulsion without the prior preparation of an organpolysiloxane/emulsifier concentrate, comprising mixing together in any desired sequence without external heating,
   A) from 10% to about 40% by weight organopolysiloxane relative to the weight of said microemulsion;
   B) an emulsifier comprising diethylene glycol monobutyl ether;
   C) water;
   D) optionally, a cosurfactant; and
   E) optionally, acid.

2. The process as claimed in claim 1, wherein the organopolysiloxane (A) employed is an organopolysiloxane of the formula $$R_nR'_mSiO_{(4-n-m)/2} \quad (I)$$

wherein
   R are identical or different, optionally substituted hydrocarbon radicals or hydrocarbonoxy radicals having in each case 1 to 18 carbon atoms,
   R' are identical or different Si-C-bonded substituted hydrocarbon radicals containing polar groups, or hydroxyl groups,
   n is an integer having a value of 0, 1, 2 or 3 and
   m is an integer having a value of 0, 1, 2 or 3, and the sum of n+m has an average value of 1.8 to 2.2 and m is chosen such that the organopolysiloxane contains at least one radical R'.

3. The process as claimed in claim 2, wherein the radicals R' are radicals of the formula $$-R^1-[NR^2(CH_2)_a]_bNHR^2, \quad (II),$$

in which
   $R^1$ is a divalent $C_1$- to $C_{18}$-hydrocarbon radical,
   $R^2$ is a hydrogen atom or an optionally substituted $C_1$-to $C_{18}$-hydrocarbon radical,
   has the values 2, 3, 4, 5 or 6 and
   has the values 0, 1, 2, 3 or 4.

4. The process of claim 1, wherein said cosurfactant (D) is present in an amount of up to about 15 weight percent based on the total weight of the emulsion.

5. The process of claim 1 wherein said cosurfactant (D) is present in an amount of up to about 10 weight percent based on the total weight of the emulsion.

6. The process of claim 4 wherein said cosurfactant (D) is selected from the group consisting of $C_5$-$C_8$ 1-alkanols, glycerol, propyl acetate, butyl acetate, pentyl acetate, and 2-pentanone.

7. The process of claim 5 wherein said cosurfactant (D) is selected from the group consisting of $C_5$-$C_8$ 1-alkanols, glycerol, propyl acetate, butyl acetate, pentyl acetate, and 2-pentanone.

8. The process of claim 6 wherein said cosurfactant (D) is selected from the group consisting of 1-pentanol, 1-hexanol, 1-octanol, and glycerol.

9. The process of claim 7 wherein said cosurfactant (D) is selected from the group consisting of 1-pentanol, 1-hexanol, 1-octanol, and glycerol.

10. A process for the preparation of an organopolysiloxane microemulsion without the prior preparation of an organpolysiloxane/emulsifier concentrate, in which the components (A) organopolysiloxane, (B) emulsifier, (C) water, optionally, (D) cosurfactant and optionally (E) acid are brought together and mixed in any desired sequence without external heating at a temperature of from 10° to about 30° C. wherein said organopolysiloxane A is present in an amount of from 10 weight percent to about 40 weight percent based on the weight of said microemulsion, and wherein said emulsifier comprises diethylene glycol monobutyl ether.

11. The process as claimed in claim 10,
wherein the organopolysiloxane (A) employed is an organopolysiloxane of the formula:

$$R_nR'_mSiO_{(4-n-m)/2} \quad (I)$$

wherein
   R are identical or different, optionally substituted hydrocarbon radicals or hydrocarbonoxy radicals having in each case 1 to 18 carbon atoms,
   R' are identical or different Si-C-bonded substituted hydrocarbon radicals containing polar groups, or hydroxyl groups,
   n is an integer having a value of 0, 1, 2 or 3 and
   m is an integer having a value of 0, 1, 2 or 3, and the sum of n+m has an average value of 1.8 to 2.2 and m is chosen such that the organopolysiloxane contains at least one radical R'.

12. The process as claimed in claim 11, wherein the radicals R' are radicals of the formula:

$$-R^1-[NR^2(CH_2)_a]_bNHR^2, \quad (II)$$

in which:

$R^1$ is a divalent $C_1$- to $C_{18}$-hydrocarbon radical, $R^2$ is a hydrogen atom or an optionally substituted $C_1$- to $C_{18}$-hydrocarbon radical, a has the values 2, 3, 4, 5 or 6 and has the values 0, 1, 2, 3 or 4.

13. The process of claim 10 wherein said cosurfactant (D) is present in an amount of up to about 15 weight percent based on the total weight of the emulsion.

14. The process of claim 10 wherein said cosurfactant (D) is present in an amount of up to about 10 weight percent based on the total weight of the emulsion.

15. The process of claim 13 wherein said cosurfactant (D) is selected from the group consisting of $C_5$-$C_8$ 1-alkanols, glycerol, propyl acetate, butyl acetate, pentyl acetate, and 2-pentanone.

16. The process of claim 14 wherein said cosurfactant (D) is selected from the group consisting of $C_5$-$C_8$ 1-alkanols, glycerol, propyl acetate, butyl acetate, pentyl acetate, and 2pentanone.

17. The process of claim 15 wherein said cosurfactant (D) is selected from the group consisting of 1-pentanol, 1-hexanol, 1-octanol, and glycerol.

18. The process of claim 16 wherein said cosurfaetant (D) is selected from the group consisting of 1-pentanol, 1-hexanol, 1-octanol, and glycerol.

19. An organopolysiloxane microemulsion comprising:

A) from 10 weight percent to about 40 weight percent of organopolysiloxane based on the weight of said microemulsion;

B) an emulsifier comprising diethylene glycol monobutyl ether;

C) water;

D) optionally, a cosurfactant; and

E) optionally, an acid.

20. An organopolysiloxane microemulsion comprising:

A) from 10 weight percent to about 40 weight percent of organopolysiloxane based on the weight of said microemulsion;

B) an emulsifier comprising diethylene glycol monobutyl ether;

C) water;

D) optionally, a cosurfactant;

E) optionally, an acid; and wherein said organopolysiloxane microemulsion is prepared by the process of claim 1.

21. The microemulsion of claim 20 wherein said water comprises minimally about 31 weight percent of said microemulsion.

UNITED STATES PATENT AND TRADEMARK OFFICE
CERTIFICATE OF CORRECTION

PATENT NO. : 5,712,343
DATED : January 27, 1998
INVENTOR(S) : MICHAEL GECK, et al.

It is certified that error appears in the above-identified patent and that said Letters Patent is hereby corrected as shown below:

```
Column 10, line 12, claim 3,
               insert "a" before "has the values . . ."

Column 10, line 13, claim 3,
               insert "b" before "has the values . . ."

Column 11, line 7, claim 12,
               insert "b" before "has the values . . ."

Column 11, line 25, claim 18,
               delete "cosurfaetant" and insert --cosurfactant--.
```

Signed and Sealed this

Seventeenth Day of November, 1998

Attest:

BRUCE LEHMAN

*Attesting Officer*  *Commissioner of Patents and Trademarks*